US009907909B2

(12) United States Patent
Finan et al.

(10) Patent No.: US 9,907,909 B2
(45) Date of Patent: Mar. 6, 2018

(54) METHOD AND SYSTEM FOR A HYBRID CONTROL-TO-TARGET AND CONTROL-TO-RANGE MODEL PREDICTIVE CONTROL OF AN ARTIFICIAL PANCREAS

(71) Applicants: Daniel Finan, Philadelphia, PA (US); Thomas McCann, Pottstown, PA (US)

(72) Inventors: Daniel Finan, Philadelphia, PA (US); Thomas McCann, Pottstown, PA (US)

(73) Assignee: Animas Corporation, West Chester, PA (US)

( * ) Notice: Subject to any disclaimer, the term of this patent is extended or adjusted under 35 U.S.C. 154(b) by 342 days.

(21) Appl. No.: 13/722,329

(22) Filed: Dec. 20, 2012

(65) Prior Publication Data

US 2014/0180240 A1  Jun. 26, 2014

(51) Int. Cl.
*A61M 31/00* (2006.01)
*A61M 5/172* (2006.01)
*G06F 19/00* (2018.01)
*A61M 5/142* (2006.01)

(52) U.S. Cl.
CPC ...... *A61M 5/1723* (2013.01); *A61M 5/14244* (2013.01); *G06F 19/3437* (2013.01); *G06F 19/3468* (2013.01); *A61M 2205/3576* (2013.01)

(58) Field of Classification Search
CPC ........ A61M 2005/1726; A61M 5/1723; A61M 5/14244; A61M 2205/3576; G06F 19/3468; G06F 19/3437
USPC .............................. 604/66, 504, 506; 706/52
See application file for complete search history.

(56) References Cited

U.S. PATENT DOCUMENTS

| 4,055,175 A | 10/1977 | Clemens et al. |
| 4,280,494 A | 7/1981 | Cosgrove, Jr. et al. |
| 5,283,729 A | 2/1994 | Lloyd |
| 5,298,022 A | 3/1994 | Bernardi |
| 5,347,446 A | 9/1994 | Iino et al. |

(Continued)

FOREIGN PATENT DOCUMENTS

| CN | 102197304 A | 9/2011 |
| CN | 102667787 A | 9/2012 |

(Continued)

OTHER PUBLICATIONS

Benyamin Grosman et al: "Zone Model Predictive Control: A Strategy to Minimize Hyper-and Hypoglycemic Events Corresponding Author", Journal of Diabetes Science and Technology Volume Diabetes Technology Society, vol. 4, No. 4, Jul. 1, 2010 (Jul. 1, 2010), pp. 961-975, XP055102711.

(Continued)

*Primary Examiner* — Kevin C Sirmons
*Assistant Examiner* — Tiffany Legette-Thompson

(57) ABSTRACT

Described and illustrated is a system for management of diabetes that includes an infusion pump, glucose sensor and controller with a method programmed into the controller. The infusion pump is configured to deliver insulin to a subject. The glucose sensor is configured to sense glucose levels in the subject and provide output signals representative of the glucose levels in the subject. The controller is programmed to switchover from one mode of MPC control based on a predetermined range of blood glucose values to another MPC mode based on a predetermined target.

18 Claims, 6 Drawing Sheets

(56) References Cited

U.S. PATENT DOCUMENTS

| | | | |
|---|---|---|---|
| 5,822,715 A * | 10/1998 | Worthington | G09B 19/00 235/375 |
| 7,060,059 B2 | 6/2006 | Keith et al. | |
| 7,276,029 B2 | 10/2007 | Goode, Jr. et al. | |
| 7,451,004 B2 | 11/2008 | Thiele et al. | |
| 7,577,483 B2 | 8/2009 | Fan et al. | |
| 8,046,089 B2 | 10/2011 | Renfro et al. | |
| 2004/0152622 A1 * | 8/2004 | Keith et al. | 514/3 |
| 2008/0103447 A1 * | 5/2008 | Reggiardo | A61M 5/14244 604/131 |
| 2008/0183060 A1 * | 7/2008 | Steil | A61B 5/14532 600/365 |
| 2008/0208113 A1 | 8/2008 | Damiano et al. | |
| 2010/0057043 A1 | 3/2010 | Kovatchev et al. | |
| 2010/0179768 A1 | 7/2010 | Kovatchev et al. | |
| 2010/0295686 A1 * | 11/2010 | Sloan et al. | 340/573.1 |
| 2011/0208156 A1 | 8/2011 | Doyle, III et al. | |
| 2011/0257496 A1 | 10/2011 | Terashima et al. | |
| 2011/0257627 A1 | 10/2011 | Hovorka | |
| 2011/0264378 A1 | 10/2011 | Breton et al. | |
| 2011/0313390 A1 * | 12/2011 | Roy | A61M 5/158 604/500 |
| 2011/0313680 A1 | 12/2011 | Doyle, III et al. | |
| 2012/0059353 A1 | 3/2012 | Kovatchev et al. | |
| 2012/0078067 A1 | 3/2012 | Kovatchev et al. | |
| 2012/0123234 A1 | 5/2012 | Atlas et al. | |
| 2012/0130698 A1 | 5/2012 | Kovatchev et al. | |
| 2012/0191361 A1 | 7/2012 | Kovatchev et al. | |
| 2012/0245556 A1 | 9/2012 | Kovatchev et al. | |
| 2012/0246106 A1 | 9/2012 | Atals et al. | |

FOREIGN PATENT DOCUMENTS

| | | |
|---|---|---|
| JP | 2012086032 A | 5/2012 |
| JP | 2012519018 A | 8/2012 |
| WO | 2011100624 A1 | 8/2011 |
| WO | 2012033734 A2 | 3/2012 |
| WO | 2012051344 A2 | 4/2012 |
| WO | 2012058694 A2 | 5/2012 |

OTHER PUBLICATIONS

Harvey R A et al: "Quest for the Artificial Pancreas: Combining Technology with Treatment", IEEE Engineering in Medicine and Biology Magazine, IEEE Service Center, Pisacataway, NJ, US, vol. 29, No. 2, Mar. 1, 2010 (Mar. 1, 2010), pp. 53-62, XP011328259, ISSN: 0739-5175, DOI:10.1109/MEMB.2009.935711.

Patek S D et al: "Modular Closed-Loop Control of Diabetes", IEEE Transactions on Biomedical Engineering, IEEE Service Center, Piscataway, NJ, USA, vol. 59, No. 11, Nov. 1, 2012 (Nov. 1, 2012), pp. 2986-2999, XP011490242, ISSN: 0018-9294, DOI:10.1109/TBME.2012.2192930.

Joe Qin S et al: "A survey of industrial model predictive control technology", Control Engineering Practice, Pergamon Press, Oxford, GB, vol. 11, Jan. 1, 2003 (Jan. 1, 2003), pp. 733-764, XP002435295, ISSN: 0967-0661, DOI:10.1016/S0967-0661(02)00186-7.

Roman Hovorka et a l: "Nonlinear model predictive control of glucose concentration in subjects with type 1 diabetes; Controlling glucose", Physiological Measurement, Institute of Physics Publishing, Bristol, GB, vol. 25. No. 4, Aug. 1, 2004 (Aug. 1, 2004), pp. 905-920, XP020074167, ISSN: 0967-3334, DOI:10.1088/0967-3334/25/4/010.

International Search Report and Written Opinion issued in related International Patent Application No. PCT/US2013/075617, dated Aug. 18, 2014, 13 pages.

Percival et al., "Closed-Loop Control and Advisory Mode Evaluation of an Artificial Pancreatic β Cell: Use of Proportional-Integral-Derivative Equivalent Model-Based Controllers" Journal of Diabetes Science and Technology, vol. 2, Issue 4, Jul. 2008.

Paola Soru et al., "MPC Based Artificial Pancreas; Strategies for Individualization and Meal Compensation" Annual Reviews in Control 36, p. 118-128 (2012).

Cobelli et al., "Artificial Pancreas: Past, Present, Future" Diabetes vol. 60, Nov. 2011.

Magni et al., "Run-to-Run Tuning of Model Predictive Control for Type 1 Diabetes Subjects: In Silico Trial" Journal of Diabetes Science and Technology, vol. 3, Issue 5, Sep. 2009.

Lee et al., "A Closed-Loop Artificial Pancreas Using Model Predictive Control and a Sliding Meal Size Estimator" Journal of Diabetes Science and Technology, vol. 3, Issue 5, Sep. 2009.

Lee et al., "A Closed-Loop Artificial Pancreas based on MPC: Human Friendly Identification and Automatic Meal Disturbance Rejection" Proceedings of the 17th World Congress, The International Federation of Automatic Control, Seoul Korea Jul. 6-11, 2008.

Magni et al., "Model Predictive Control of Type 1 Diabetes: An in Silico Trial" Journal of Diabetes Science and Technology, vol. 1, Issue 6, Nov. 2007.

Wang et al., "Automatic Bolus and Adaptive Basal Algorithm for the Artificial Pancreatic β-Cell" Diabetes Technology and Therapeutics, vol. 12, No. 11, 2010.

Percival et al., "Closed-Loop Control of an Artificial Pancreatic β-Cell Using Multi-Parametric Model Predictive Control" Diabetes Research 2008.

Kovatchev et al., "Control to Range for Diabetes: Functionality and Modular Architecture" Journal of Diabetes Science and Technology, vol. 3, Issue 5, Sep. 2009.

Atlas et al., "MD-Logic Artificial Pancreas System" Diabetes Care, vol. 33, No. 5, May 2010.

Maciejowski JM, "Predictive Control with Constraints", Harlow, UK: Prentice-Hall, Pearson Education Limited, 2002.

Rachel Gillis et al., "Glucose Estimation and Prediction through Meal Responses Using Ambulatory Subject Data for Advisory Mode Model Predictive Control" Journal of Diabetes Science and Technology vol. 1, Issue 6, Nov. 2007.

Youqing Wang et al., "Closed-Loop Control of Artificial Pancreatic β-Cell in Type 1 Diabetes Mellitus Using Model Predictive Iterative Learning Control" IEEE Transactions on Biomedical Engineering, vol. 57, No. 2, Feb. 2010.

Alejandro H. Gonzalez et al., "A stable MPC with zone control," Science Direct, Journal of Process Control 19 (2009) 110-122.

Johannes Plank et al., "Multicentric, Randomized, Controlled Trial to Evaluate Blood Glucose Control by the Model Predictive Control Algorithm Versus Routine Glucose Management Protocols in Intensive Care Unit Patients," Diabetes Care, vol. 29, No. 2, Feb. 2006, 271-276.

Rishi Amrit, "Optimizing Process Economics in Model Predictive Control," University of Wisconsin—Madison, Dissertation, 2011, 193 pages.

Bruce Buckingham, "Update on Closed-Loop Therapies," Stanford Medical Center, Presentation, 123 pages.

Compute MPC control law—Simulink, "MPC Controller," http://www.mathworks.com/help/mpc/ref/mpccontroller.html, printed Nov. 19, 2012, 8 pages.

Eric C. Kerrigan et al., "Feedback min-max model predictive control using a single linear program: Robust stability and the explicit solution," Int. J. Robust Nonlinear Control 2004; 14:395-413.

Marc Breton et al., "Fully Integrated Artificial Pancreas in Type 1 Diabetes Modular Closed-Loop Glucose Control Maintains Near Normoglycemia," Diabetes Publish Ahead of Print, published online Jun. 11, 2012, diabetes. diabetesjournals.org.

Thomas Haugan, "Diploma Thesis Real-Time Model Predictive Control," Swiss Federal Institute of Technology, Jun. 13, 2001, 117 pages.

B. Wayne Bequette, "Analysis of Algorithms for Intensive Care Unit Blood Glucose Control," Journal of Diabetes Science and Technology, vol. 1, Issue 6, Nov. 2007, 813-824.

Emad Ali, "Heuristic On-Line Tuning for Nonlinear Model Predictive Controllers Using Fuzzy Logic," J Process Control, 13(5), 383-396, 2003.

(56) References Cited

OTHER PUBLICATIONS

Hiroaki Fukushima et al., "Robust Constrained Model Predictive Control using Closed-loop Prediction," Kyoto University, 29 pages.
Honeywell, "Closed Loop Identification for Model Predictive Control: Application to Air Separation Process," Aug. 2011, 8 pages.
Raul Shridhar et al., "A Tuning Strategy for Unconstrained Multivariable Model Predictive Control," Ind. Eng. Chem. Res. 1998, 37, 4003-4016.
Alejandro H. Gonzalez et al., "Robust Model Predictive Control for Time Delayed Systems with Optimizing Targets and Zone Control," Robust Control, Theory and Applications, ISBN: 978-953-307-229-6, InTech (2011), 339-370.
L.R.E. Shead et al., "Conditions for which linear MPC converges to the correct target," Journal of Process Control 20( 2010) 1243-1251.
Morten Hovd, "Improved Target Calculation for Model Predictive Control," Modeling, Identification and Control, vol. 28, No. 3, 2007, 81-86.
Bradley Anderson et al., "Model Predictive Control," ControlsWiki, 2006, https://controls.engin.umich.edu/wiki/index.php/MPC, 13 pages.
K. S. Holkar et al., "An Overview of Model Predictive Control," International Journal of Control and Automation, vol. 3, No. 4, Dec. 2010, 47-64.
MPC tools Algorithm Details, "Model Predictive Control Tools Package, MPC Tools: How does it work?" from http://jbrwww.che.wisc.edu/software/mpctools/method.html, printed Nov. 19, 2012, 2 pages.
Rishi Amrit et al., "Nonlinear Model Predictive Control Tools," Apr. 5, 2008, 12 pages.
Yuval Tassa et al., "Fast Model Predictive Control for Reactive Robotic Swimming," 7 pages.
Christian Ellingsen et al., "Safety Constraints in an Artificial Pancreatic β Cell: An Implementation of Model Predictive Control with Insulin and Blood," Journal of Diabetes Science and Technology, vol. 3, Issue 3, May 2009, 536-544.
D. Q. Mayne et al., "Constrained model predictive control: Stability and optimality," Automatica 36 (2000) 789-814.
M. A. Zermani et al., "Self-tuning weighting factor to decoupling control for incubator system," International Journal of Information Technology, Control and Automation (IJITCA) vol. 2, No. 3, Jul. 2012, 67-83.
Matthew J. Tenny et al., "Closed-loop Behavior of Nonlinear Model Predictive Control," TWMCC Technical Report Apr. 2002, 32 pages.
William L. Clarke et al., "Closed-Loop Artificial Pancreas Using Subcutaneous Glucose Sensing and Insulin Delivery and a Model Predictive Control Algorithm: The Virginia Experience," Journal of Diabetes Science and Technology, vol. 3, Issue 5, Sep. 2009, 1031-1032.
Boris Kovatchev et al., "Multinational Study of Subcutaneous Model-Predictive Closed-Loop Control in Type 1 Diabetes Mellitus: Summary of the Results," Journal of Diabetes Science and Technology, vol. 4, Issue 6, Nov. 2010, 1374-1381.
Presentation of "Model Predictive Control (MPC)," 49 pages.
International Preliminary Report on Patentability issued in related International Patent Application No. PCT/US2013/075617, dated Jun. 23, 2015, 8 pages.
Search Report issued in related Japanese Patent Application No. 201380067221.4, dated Feb. 16, 2017, 3 pages.
First Office Action issued in related Japanese Patent Application No. 201380067221.4, dated Feb. 28, 2017, 24 pages.
Notification of Reasons for Refusal issued in corresponding Japanese Patent Application No. 2015-549555, dated Sep. 19, 2017, 10 pages (with English translation).

* cited by examiner

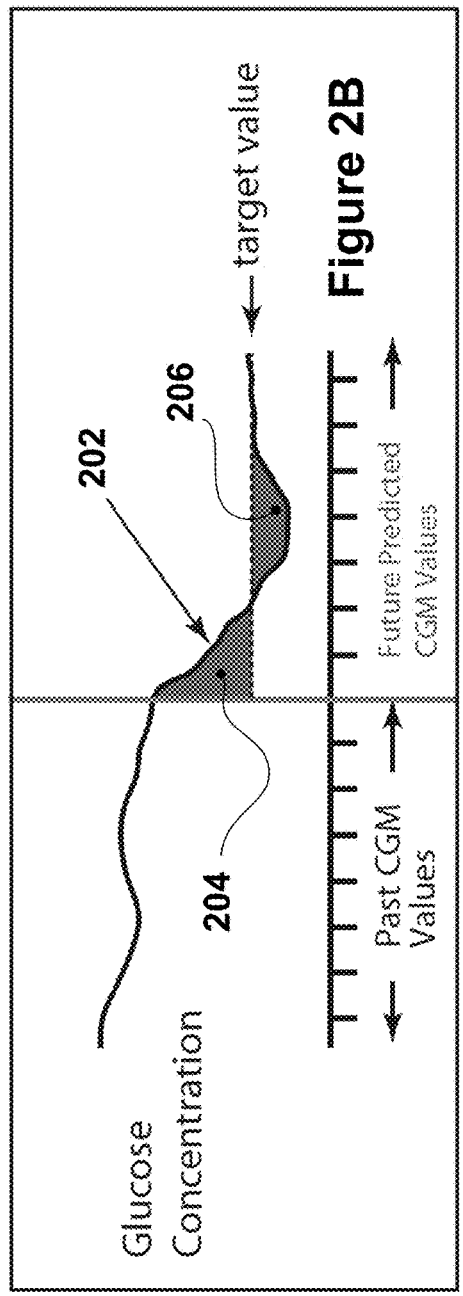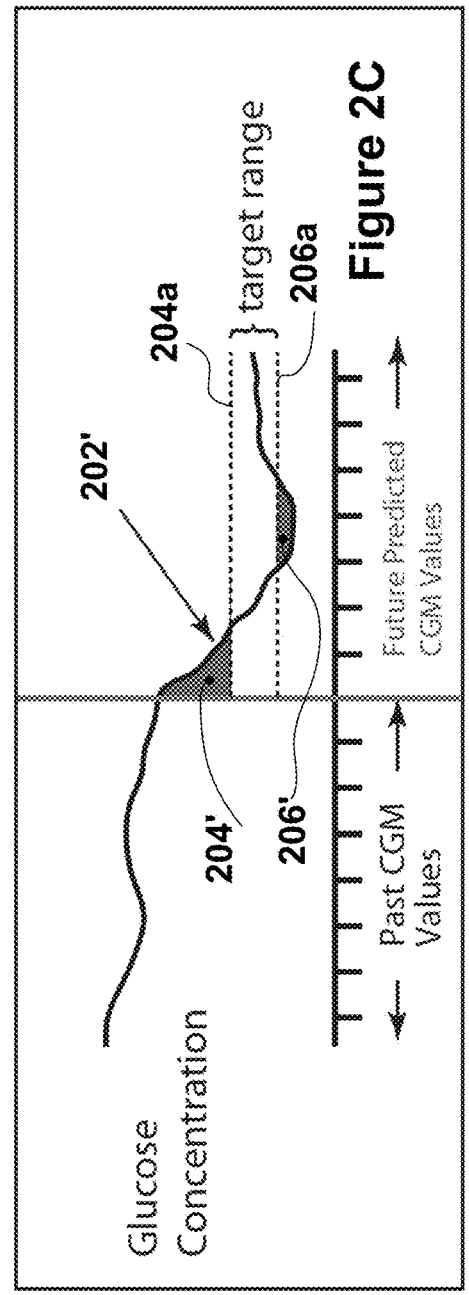

METHOD AND SYSTEM FOR A HYBRID CONTROL-TO-TARGET AND CONTROL-TO-RANGE MODEL PREDICTIVE CONTROL OF AN ARTIFICIAL PANCREAS

BACKGROUND

Diabetes mellitus is a chronic metabolic disorder caused by an inability of the pancreas to produce sufficient amounts of the hormone insulin, resulting in the decreased ability of the body to metabolize glucose. This failure leads to hyperglycemia, i.e. the presence of an excessive amount of glucose in the blood plasma. Persistent hyperglycemia and/or hypoinsulinemia has been associated with a variety of serious symptoms and life threatening long term complications such as dehydration, ketoacidosis, diabetic coma, cardiovascular diseases, chronic renal failure, retinal damage and nerve damages with the risk of amputation of extremities. Because restoration of endogenous insulin production is not yet possible, a permanent therapy is necessary which provides constant glycemic control in order to always maintain the level of blood glucose within normal limits. Such glycemic control is achieved by regularly supplying external insulin to the body of the patient to thereby reduce the elevated levels of blood glucose.

External biologic such as insulin was commonly administered by means of multiple daily injections of a mixture of rapid and intermediate acting drugs via a hypodermic syringe. It has been found that the degree of glycemic control achievable in this way is suboptimal because the delivery is unlike physiological hormone production, according to which hormone enters the bloodstream at a lower rate and over a more extended period of time. Improved glycemic control may be achieved by the so-called intensive hormone therapy which is based on multiple daily injections, including one or two injections per day of a long acting hormone for providing basal hormone and additional injections of a rapidly acting hormone before each meal in an amount proportional to the size of the meal. Although traditional syringes have at least partly been replaced by insulin pens, the frequent injections are nevertheless very inconvenient for the patient, particularly those who are incapable of reliably self-administering injections.

Substantial improvements in diabetes therapy have been achieved by the development of the drug delivery device, relieving the patient of the need for syringes or drug pens and the administration of multiple daily injections. The drug delivery device allows for the delivery of drug in a manner that bears greater similarity to the naturally occurring physiological processes and can be controlled to follow standard or individually modified protocols to give the patient better glycemic control.

In addition, delivery directly into the intraperitoneal space or intravenously can be achieved by drug delivery devices. Drug delivery devices can be constructed as an implantable device for subcutaneous arrangement or can be constructed as an external device with an infusion set for subcutaneous infusion to the patient via the transcutaneous insertion of a catheter, cannula or a transdermal drug transport such as through a patch. External drug delivery devices are mounted on clothing, hidden beneath or inside clothing, or mounted on the body and are generally controlled via a user interface built-in to the device or on a separate remote device.

Blood or interstitial glucose monitoring is required to achieve acceptable glycemic control. For example, delivery of suitable amounts of insulin by the drug delivery device requires that the patient frequently determines his or her blood glucose level and manually inputs this value into a user interface for the external pumps, which then calculates a suitable modification to the default or currently in-use insulin delivery protocol, i.e. dosage and timing, and subsequently communicates with the drug delivery device to adjust its operation accordingly. The determination of blood glucose concentration is typically performed by means of an episodic measuring device such as a hand-held electronic meter which receives blood samples via enzyme-based test strips and calculates the blood glucose value based on the enzymatic reaction.

Continuous glucose monitoring (CGM) has also been utilized over the last twenty years with drug delivery devices to allow for closed loop control of the insulin(s) being infused into the diabetic patients. To allow for closed-loop control of the infused insulins, proportional-integral-derivative ("PID") controllers have been utilized with mathematical model of the metabolic interactions between glucose and insulin in a person. The PID controllers can be tuned based on simple rules of the metabolic models. However, when the PID controllers are tuned or configured to aggressively regulate the blood glucose levels of a subject, overshooting of the set level can occur, which is often followed by oscillations, which is highly undesirable in the context of regulation of blood glucose.

Alternative controllers were also investigated. It was determined that a model predictive controller ("MPC") used in the petrochemical industries where processes involved large time delays and system responses, was the most suitable for the complex interplay between insulin, glucagon, and blood glucose. The MPC controller has been demonstrated to be more robust than PID because MPC considers the near future effects of control changes and constraints in determining the output of the MPC whereas PID typically involves only past outputs in determining future changes. Constraints can be implemented in the MPC controller such that MPC prevents the system from running away when the limit has already been reached. Another benefit of MPC controllers is that the model in the MPC can, in some cases, theoretically compensate for dynamic system changes whereas a feedback control, such as PID control, such dynamic compensation would not be possible.

MPC can be viewed therefore as a combination of feedback and feedforward control. MPC, however, typically requires a metabolic model to mimic as closely as possible to the interaction between insulin and glucose in a biological system. As such, due to person-to-person biological variations, MPC models continue to be further refined and developed and details of the MPC controllers, variations on the MPC and mathematical models representing the complex interaction of glucose and insulin are shown and described in the following documents:

U.S. Pat. No. 7,060,059; US Patent Application Nos. 2011/0313680 and 2011/0257627; International Publication WO 2012/051344;

Percival et al., "*Closed-Loop Control and Advisory Mode Evaluation of an Artificial Pancreatic β Cell: Use of Proportional-Integral-Derivative Equivalent Model-Based Controllers*" Journal of Diabetes Science and Technology, Vol. 2, Issue 4, July 2008.

Paola Soru et al., "*MPC Based Artificial Pancreas; Strategies for Individualization and Meal Compensation*" Annual Reviews in Control 36, p. 118-128 (2012), Cobelli et al., "Artificial Pancreas: Past, Present, Future" Diabetes Vol. 60, November 2011;

Magni et al., "*Run-to-Run Tuning of Model Predictive Control for Type 1 Diabetes Subjects: In Silico Trial*" Journal of Diabetes Science and Technology, Vol. 3, Issue 5, September 2009.

Lee et al., "*A Closed-Loop Artificial Pancreas Using Model Predictive Control and a Sliding Meal Size Estimator*" Journal of Diabetes Science and Technology, Vol. 3, Issue 5, September 2009;

Lee et al., "*A Closed-Loop Artificial Pancreas based on MPC: Human Friendly Identification and Automatic Meal Disturbance Rejection*" Proceedings of the $17^{th}$ World Congress, The International Federation of Automatic Control, Seoul Korea Jul. 6-11, 2008;

Magni et al., "*Model Predictive Control of Type 1 Diabetes: An in Silico Trial*" Journal of Diabetes Science and Technology, Vol. 1, Issue 6, November 2007;

Wang et al., "*Automatic Bolus and Adaptive Basal Algorithm for the Artificial Pancreatic β-Cell*" Diabetes Technology and Therapeutics, Vol. 12, No. 11, 2010; and Percival et al., "*Closed-Loop Control of an Artificial Pancreatic β-Cell Using Multi-Parametric Model Predictive Control*" Diabetes Research 2008.

Kovatchev et al., "*Control to Range for Diabetes: Functionality and Modular Architecture*" Journal of Diabetes Science and Technology, Vol. 3, Issue 5, September 2009 (hereafter "Kovatchev").

Atlas et al., "*MD-Logic Artificial Pancreas System*" Diabetes Care, Volume 33, Number 5, May 2010 (hereafter "Atlas"). All articles or documents cited in this application are hereby incorporated by reference into this application as if fully set forth herein.

In this field, it was determined by Kovatchev in 2009 that a control to range, i.e., where the glucose value is maintained by the controller within a predetermined range of glucose values, was easier to implement in that the control to range only computes corrections with respect to the nominal open-loop strategy and no integral action is included while a simple linear model is used; constraints are not considered explicitly; and the aggressiveness of control actions is individualized. Thus, it is apparent that Kovatchev considers control-to-range ("CTR") to be more desirable than a control-to-target ("CTT") where the blood glucose was controlled to a fixed threshold. Despite this preference for CTR by Kovatchev, Atlas demonstrated in 2010 that a combination of CTR and CTT can be utilized to quite good efficacy in managing diabetes. Atlas, however, failed to describe or illustrate how the CTR and CTT were to be utilized in his experiments. Specifically, Atlas failed to show or describe the interplay between CTR and CTT and whether both CTR and CTT were utilized separately or concurrently.

SUMMARY OF THE DISCLOSURE

Applicants have recognized that a key requirement in the utilization of CTR and CTT is knowing when to switch from CTR to CTT and vice versa. Accordingly, applicants have devised a technique to allow a controller to utilize the appropriate technique for insulin dosing in a diabetes management system, such as, for example, an artificial pancreas.

In one aspect, a method to control an infusion pump with a model-predictive-controller and receive data from at least one glucose sensor is provided. The method can be achieved by: measuring glucose level in the subject from the glucose sensor to provide at least one glucose measurement in each time interval; predicting at least one future glucose value based on the glucose measurements made in the measuring step; evaluating whether the at least one future glucose value is within a predetermined range of glucose values, in the event the at least one future glucose value is not within the range, determining an insulin amount with the model-predictive controller based on a target value otherwise determining an insulin amount with the model-predictive-controller based on the predetermined range; and delivering the insulin in the amount determined in the determining step.

In yet another aspect, a system for management of diabetes that includes a continuous glucose sensor, an insulin infusion pump and a controller. The continuous glucose monitor is configured to continuously measure glucose level of the subject at discrete generally uniform time intervals and provide the glucose level at each interval in the form of glucose measurement data. The insulin infusion pump is configured to deliver insulin. The controller is in communication with the pump, glucose meter and the glucose monitor in which the controller is configured to predict at least one future glucose value based on prior glucose measurement data from the continuous glucose monitor, and evaluate whether the at least one future glucose value is within a predetermined range of glucose values and in the event the at least one future glucose value is not within the range, a determination is made of an insulin amount with the model-predictive controller based on a target value otherwise a determination is made of an insulin amount with the model-predictive-controller based on the predetermined range and command the insulin infusion pump to deliver the insulin amount determined by the controller.

The following features can be combined in combination with each other and with each of the above aspects. For example, the measuring may include assaying glucose values with a continuous glucose sensor; the delivering may include injecting the insulin with an insulin infusion pump.

These and other embodiments, features and advantages will become apparent to those skilled in the art when taken with reference to the following more detailed description of various exemplary embodiments of the invention in conjunction with the accompanying drawings that are first briefly described.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention (wherein like numerals represent like elements).

FIGS. 2B and 2C illustrate respective examples of conceptual costs in MPC calculations (the sum of the red areas) for an artificial pancreas application for a) control-to-target and b) control-to-range techniques.

MODES FOR CARRYING OUT THE INVENTION

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. In addition, as used herein, the terms "patient," "host," "user," and "subject" refer to any human or animal subject and are not intended to limit the systems or methods to human use, although use of the subject invention in a human patient represents a preferred embodiment. Furthermore, the term "user" includes not only the patient using a drug infusion device but also the caretakers (e.g., parent or guardian, nursing staff or home care employee). The term "drug" may include hormone, biologically active materials, pharmaceuticals or other chemicals that cause a biological response (e.g., glycemic response) in the body of a user or patient.

Figure 1:
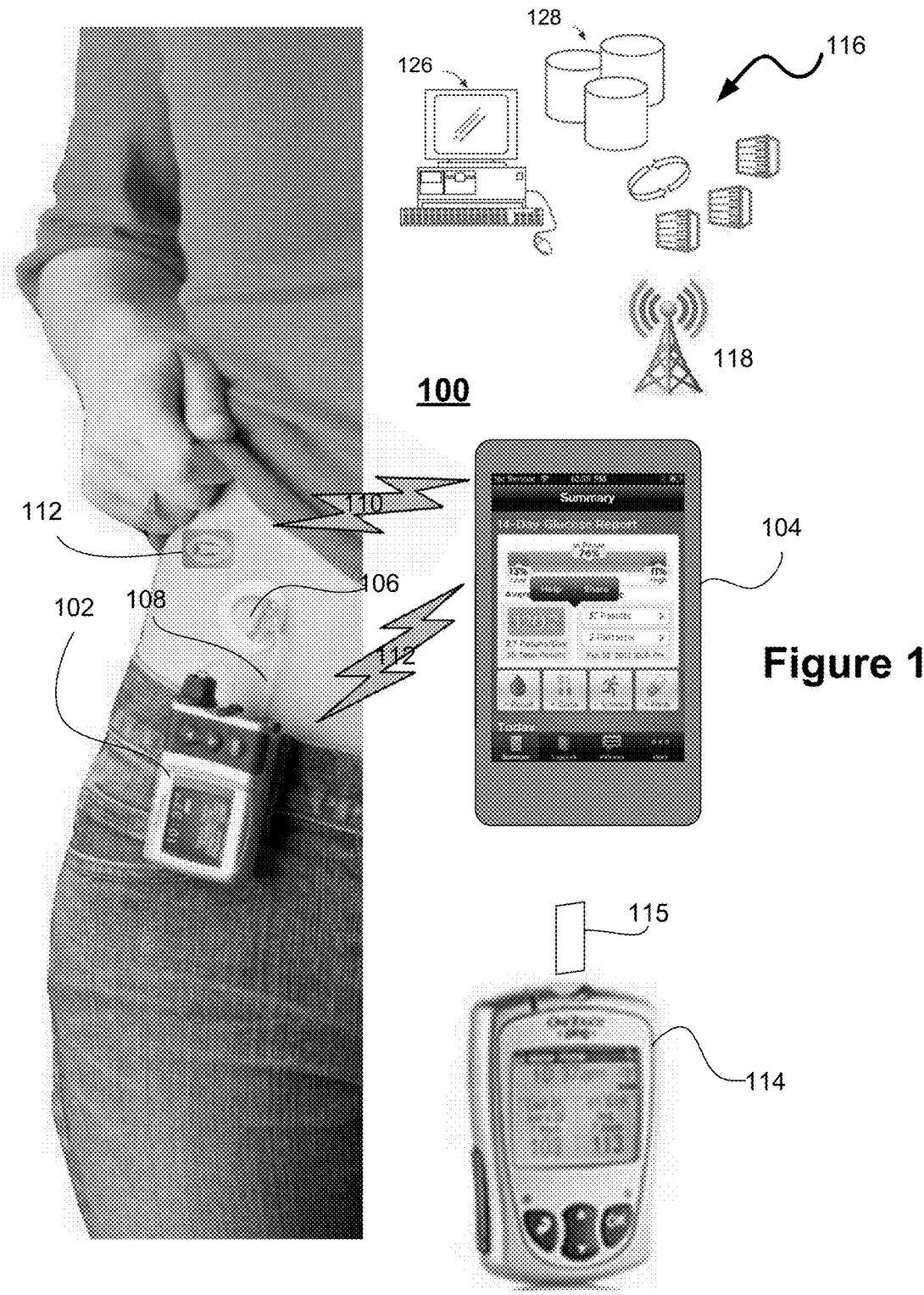
FIG. 1 illustrates the system in which a controller for the pump or glucose monitor(s) is separate from both the infusion pump and the glucose monitor(s) and in which a network can be coupled to the controller to provide near real-time monitoring.

FIG. 1 illustrates a drug delivery system 100 according to an exemplary embodiment that utilizes the principles of the invention. Drug delivery system 100 includes a drug delivery device 102 and a remote controller 104. Drug delivery device 102 is connected to an infusion set 106 via flexible tubing 108.

Drug delivery device 102 is configured to transmit and receive data to and from remote controller 104 by, for example, radio frequency communication 112. Drug delivery device 102 may also function as a stand-alone device with its own built in controller. In one embodiment, drug delivery device 102 is an insulin infusion device and remote controller 104 is a hand-held portable controller. In such an embodiment, data transmitted from drug delivery device 102 to remote controller 104 may include information such as, for example, insulin delivery data, blood glucose information, basal, bolus, insulin to carbohydrates ratio or insulin sensitivity factor, to name a few. The controller 104 is configured to include an MPC controller 10 that has been programmed to receive continuous glucose readings from a CGM sensor 112. Data transmitted from remote controller 104 to insulin delivery device 102 may include glucose test results and a food database to allow the drug delivery device 102 to calculate the amount of insulin to be delivered by drug delivery device 102. Alternatively, the remote controller 104 may perform basal dosing or bolus calculation and send the results of such calculations to the drug delivery device. In an alternative embodiment, an episodic blood glucose meter 114 may be used alone or in conjunction with the CGM sensor 112 to provide data to either or both of the controller 104 and drug delivery device 102. Alternatively, the remote controller 104 may be combined with the meter 114 into either (a) an integrated monolithic device; or (b) two separable devices that are dockable with each other to form an integrated device. Each of the devices 102, 104, and 114 has a suitable micro-controller (not shown for brevity) programmed to carry out various functionalities.

Drug delivery device 102 may also be configured for bi-directional wireless communication with a remote health monitoring station 116 through, for example, a wireless communication network 118. Remote controller 104 and remote monitoring station 116 may be configured for bi-directional wired communication through, for example, a telephone land based communication network. Remote monitoring station 116 may be used, for example, to download upgraded software to drug delivery device 102 and to process information from drug delivery device 102. Examples of remote monitoring station 116 may include, but are not limited to, a personal or networked computer 126, server 128 to a memory storage, a personal digital assistant, other mobile telephone, a hospital base monitoring station or a dedicated remote clinical monitoring station.

Drug delivery device 102 includes processing electronics: including a central processing unit and memory elements for storing control programs and operation data, a radio frequency module 116 for sending and receiving communication signals (i.e., messages) to/from remote controller 104, a display for providing operational information to the user, a plurality of navigational buttons for the user to input information, a battery for providing power to the system, an alarm (e.g., visual, auditory or tactile) for providing feedback to the user, a vibrator for providing feedback to the user, a drug delivery mechanism (e.g. a drug pump and drive mechanism) for forcing a insulin from a insulin reservoir (e.g., a insulin cartridge) through a side port connected to an infusion set 108/106 and into the body of the user.

Glucose levels or concentrations can be determined by the use of the CGM sensor 112. The CGM sensor 112 utilizes amperometric electrochemical sensor technology to measure glucose with three electrodes operably connected to the sensor electronics and are covered by a sensing membrane and a biointerface membrane, which are attached by a clip.

The top ends of the electrodes are in contact with an electrolyte phase (not shown), which is a free-flowing fluid phase disposed between the sensing membrane and the electrodes. The sensing membrane may include an enzyme, e.g., glucose oxidase, which covers the electrolyte phase. In this exemplary sensor, the counter electrode is provided to balance the current generated by the species being measured at the working electrode. In the case of a glucose oxidase based glucose sensor, the species being measured at the working electrode is $H_2O_2$. The current that is produced at the working electrode (and flows through the circuitry to the counter electrode) is proportional to the diffusional flux of $H_2O_2$. Accordingly, a raw signal may be produced that is representative of the concentration of glucose in the user's body, and therefore may be utilized to estimate a meaningful glucose value. Details of the sensor and associated components are shown and described in U.S. Pat. No. 7,276,029, which is incorporated by reference herein as if fully set forth herein this application. In one embodiment, a continuous glucose sensor from the Dexcom Seven System (manufactured by Dexcom Inc.) can also be utilized with the exemplary embodiments described herein.

In one embodiment of the invention, the following components can be utilized as a system for management of diabetes that is akin to an artificial pancreas: OneTouch Ping® Glucose Management System by Animas Corporation that includes at least an infusion pump and an episodic glucose sensor; and DexCom® SEVEN PLUS® CGM by DexCom Corporation with interface to connect these components and programmed in MATLAB® language and accessory hardware to connect the components together; and control algorithms in the form of an MPC that automatically regulates the rate of insulin delivery based on the glucose level of the patient, historical glucose measurement and anticipated future glucose trends, and patient specific information.

Figure 2A:
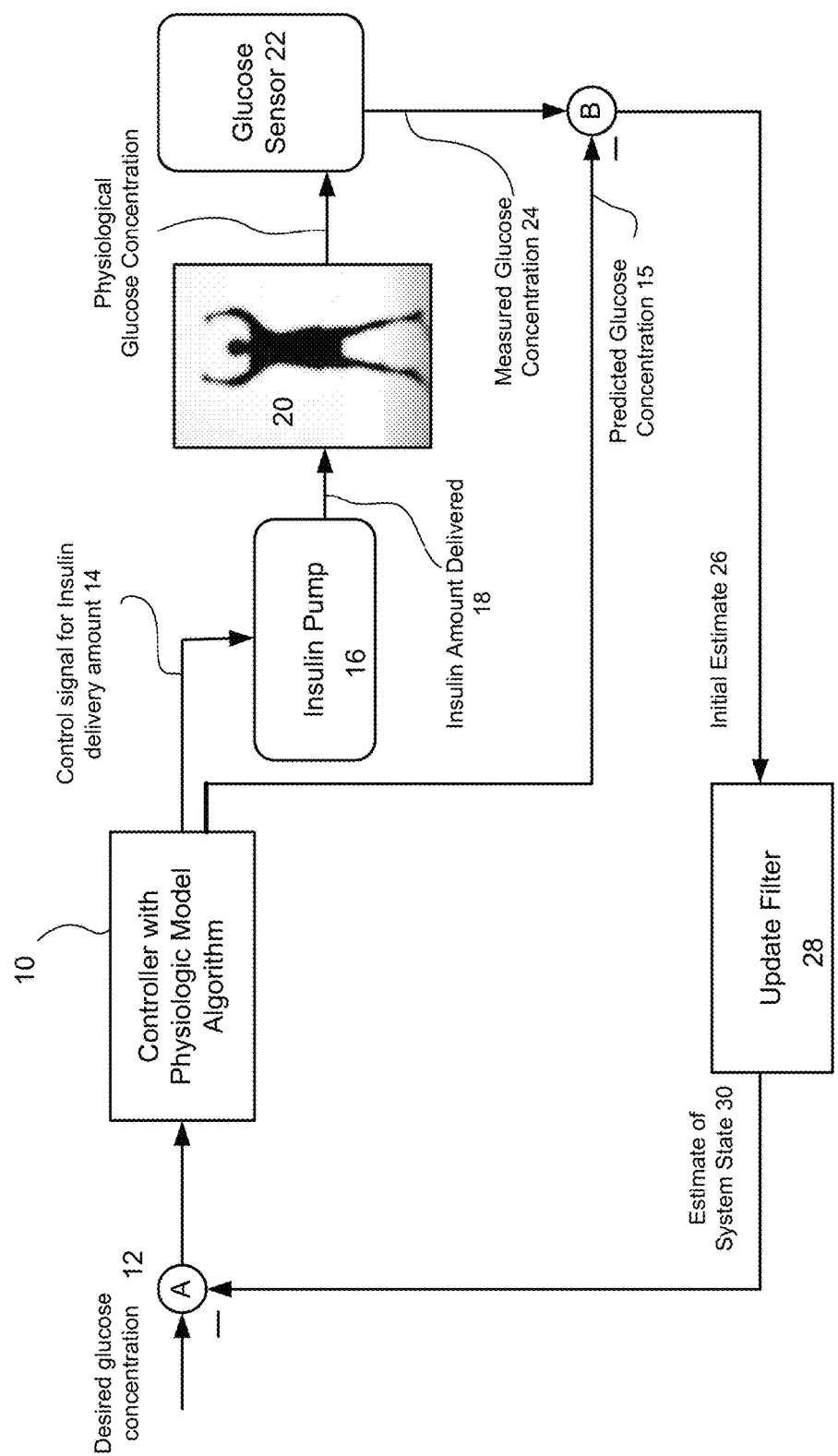
FIG. 2A illustrates an exemplary embodiment of the diabetic management system in schematic form.

FIG. 2A illustrates a schematic diagram 200 of the system 100 in FIG. 1 programmed with the solution devised by applicants to counteract a less than desirable effect of a closed-loop control system. In particular, FIG. 2A provides for an MPC programmed into a control logic module 10 that is utilized in controller 104. MPC enabled module 10 receives a desired glucose concentration or range of glucose concentration 12 (along with any modification from an update filter 28 so that it is able to maintain the output (i.e., glucose level) of the subject within the desired range of glucose levels.

Referring to FIG. 2A, the first output 14 of the MPC-enabled control logic 10 can be a control signal to an insulin pump 16 to deliver a desired quantity of insulin 18 into a subject 20 at predetermined time intervals, which can be indexed every 5 minutes using time interval index k. A second output in the form of a predicted glucose value 15 can be utilized in control junction B. A glucose sensor 22 (or 112 in FIG. 1) measures the glucose levels in the subject 20 in order to provide signals 24 representative of the actual or measured glucose levels to control junction B, which takes the difference between measured glucose concentration 24 and the MPC predictions of that measured glucose concentration. This difference provides input for the update filter 26 of state variables of the model. The difference 26 is provided to an estimator (also known as an update filter 28) that provides for estimate of state variables of the model that cannot be measured directly. The update filter 28 is preferably a recursive filter in the form of a Kalman filter with tuning parameters for the model. The output of the update or recursive filter 28 is provided to control junction A whose output is utilized by the MPC in the control logic 10 to further refine the control signal 14 to the pump 16 (or 102 in FIG. 1).

Two common automatic control techniques for MPC are known as "control-to-target," or CTT, and "control-to-range," or CTR. In both schemes, the controller attempts to drive the controlled variable(s) to desired levels by adjusting the manipulated variable(s). In a CTT scheme, the controller attempts to drive the controlled variable(s) to a specific target value, a.k.a. set point; in a CTR scheme, on the other hand, the controller attempts to keep the controlled variable(s) within a target range of values.

CTT approaches are useful for systems whose controlled variables must be maintained as close to a certain value as possible; CTR approaches, on the other hand, are useful for systems whose controlled variable can fluctuate safely between a lower and an upper limit. In the latter case, the fewer the control moves (i.e., adjustments of the manipulated variable away from its steady-state set point or target range), the better.

In some MPC frameworks, the solution to the control problem is that value (or those values) of the manipulated variable(s) that result in the smallest predicted conceptual "cost" for the future. An example of a "cost" is the predicted deviation of the controlled variable away from the desired level. More specifically, it could be the absolute integral of the predicted trajectory of the controlled variable away from the set point (in the case of CTT), or outside of the acceptable range (in the case of CTR). An illustration of these two cases for an artificial pancreas application (although the methodology can be applied to many controlled variables) is shown in FIGS. 2B and 2C.

In FIG. 2B, the glucose prediction from the CTT-MPC model is 202, the dashed line 204 is the target value and the cost is the sum of the shaded areas 204 and 206. In FIG. 2C, which is for a CTR-MPC technique, the dashed lines 204a and 204b represent the range or zone in which a prediction of future glucose 202' must be within this zone. Similar to the CTT-MPC technique in FIG. 2B, the cost in the CTR-MPC model in FIG. 2C is the shaded areas 204' and 206'. In the respective MPC techniques, a second conceptual cost might be the analogous deviation of the manipulated variable(s) away from its steady-state set point or target range. Assigning such a cost to this deviation is a way of preventing absolute reliance on the measurements of the controlled variable, an important safeguard in applications for which there is known inaccuracy in the sensor (e.g., CGM noise, drift, and/or RF communication issues). It is noted that, compared to the CTT approach, the CTR approach can result in more difficult computations. In applications in which computation capacity and speed are at a premium, as in embedded systems, the increased computation load can become an issue.

Applicants have recognized the advantages of each technique and therefore have devised a heretofore novel technique to determine when each technique is most suitable in the context of an artificial pancreas system. Each technique will be discussed briefly below, starting with the CTR technique.

Control-to-Range MPC Mode.

The MPC logic is formulated to control a subject glucose level to a safe glucose zone, with the lower blood glucose limit of the zone varying between 80-100 mg/dL and the upper blood glucose limit varying between about 140-180 mg/dL; the algorithm will henceforth be referred to as the "Zone MPC". Controlling to a target zone is, in general, applied to controlled systems that lack a specific set point with the controller's goal being to keep the controlled variable (CV) in a predefined zone. Control to zone (i.e., a normaglycemic zone) is highly suitable for the artificial pancreas because of the absence of a natural glycemic set point. Moreover, an inherent benefit of control to zone is the ability to limit pump actuation/activity in a way that if glucose levels are within the zone then no extra correction shall be suggested.

In real-time, the insulin delivery rate $I_D$ from the Zone MPC law is calculated by an on-line optimization, which evaluates at each sampling time the next insulin delivery rate. The optimization at each sampling time is based on the estimated metabolic state (plasma glucose, subcutaneous insulin) obtained from the dynamic model stored in module 10.

The MPC of control logic 10 incorporates an explicit model of human T1DM glucose-insulin dynamics. The model is used to predict future glucose values and to calculate future controller moves that will bring the glucose profile to the desired range or "Zone." MPC in controllers can be formulated for both discrete- and continuous-time systems; the controller is set in discrete time, with the discrete time (stage) index k referring to the epoch of the $k^{th}$ sample occurring at continuous time $t=k \cdot T_s$, where $T_s=5$ min is the sampling period. Software constraints ensure that insulin delivery rates are constrained between minimum (i.e., zero) and maximum values. The first insulin infusion (out of N steps) is then implemented. At the next time step, k+1 based on the new measured glucose value and the last insulin rate, the process is repeated.

Specifically, we start with the original linear difference model used for Zone MPC:

$$G'(k)=a_1G(k-1)+a_2G'(k-2)+a_3G'(k-3)+a_4G'(k-4)+a_5G'(k-5)+bI_M(k-4)I_M(k)=c_1I_M(k-1)+c_2I_M(k-2)+d_1I'_D(k-1)+d_2I'_D(k-2) \quad \text{Eq. (1)}$$

where:
k is the discrete time interval index having a series of indexing counters where k=1, 2, 3 . . . .
G' is the measured glucose concentration
$I_M$ is the "mapped insulin" which is not a measured quantity
$I'_D$ is the delivered insulin or a manipulated variable
and coefficients $a_1$~2.993; $a_2$~(−3.775); $a_3$~2.568; $a_4$~(−0.886); $a_5$~0.09776; b~(−1.5); $c_1$~1.665; $c_2$~(−0.693); $d_1$~0.01476; $d_2$~0.01306.

Using the FDA accepted metabolic simulator known to those skilled in the art, Eq. (1) can be reduced to the following linear difference model in Equation (2):

$$\begin{aligned}
(a) \quad G'(k) &= 2.993G'(k-1) - 3.775G'(k-2) + \\
&\quad 2.568G'(k-3) - 0.886G'(k-4) + \\
&\quad 0.09776G'(k-5) - \\
&\quad 1.5I_M(k-4) + \\
&\quad 0.1401\text{Meal}_M(k-2) + 1.933\text{Meal}_M(k-3) \\
(b) \quad I_M(k) &= 1.665I_M(k-1) - 0.693I_M(k-2) + \\
&\quad 0.01476I'_D(k-1) + 0.01306I'_D(k-2) \\
(c) \quad \text{Meal}_M(k) &= 1.501\text{Meal}_M(k-1) + \\
&\quad 0.5427\text{Meal}_M(k-2) + \\
&\quad 0.02279\text{Meal}(k-1) + 0.01859\text{Meal}(k-2)
\end{aligned} \quad (2)$$

where:
G' is the glucose concentration output (G) deviation variable (mg/dL), i.e., G'≡G−110 mg/dL,
$I_D$' is the insulin infusion rate input ($I_D$) deviation variable (U/h), i.e., $I_D$'≡$I_D$−basal U/h,
Meal is the CHO ingestion input (gram-CHO),
$I_M$ is the mapped subcutaneous insulin infusion rates (U/h), and
Meal$_M$ is the mapped CHO ingestion input (gram-CHO).

The dynamic model in Eq. (2) relates the effects of insulin infusion rate ($I_D$), and CHO ingestion input (Meal) on plasma glucose. The model represents a single average model for the total population of subjects. The model and its parameters are fixed.

The second-order input transfer functions described by parts (b) and (c) in Eq. (2) are used to generate an artificial input memory in the Zone MPC schema to prevent insulin over-dosing, and consequently prevent hypoglycemia. In order to avoid over-delivery of insulin, the evaluation of any sequential insulin delivery must take into consideration the past administered insulin against the length of the insulin action. However, a one-state linear difference model with a relatively low order uses the output (glycemia) as the main source of past administered input (insulin) "memory." In the face of the model mismatch, noise, or change in the subject's insulin sensitivity, this may result in under- or over-delivery of insulin. This is mitigated by adding two additional states ($I_M$ and Meal$_M$) for the mapped insulin and meal inputs that carry a longer insulin memory.

The CTR technique in the context of zone MPC ("Zone MPC") is applied when the specific set point value of a controlled variable ("CV") (in the form of glucose value) is of low relevance compared to a zone that is defined by upper and lower boundaries or a range of the CV. Moreover, in the presence of noise and model mismatch there is no practical value using a fixed set point. Zone MPC was developed through research by the University of California at Santa Barbara and the Sansom Diabetes Research Institute. Other details of the derivation for the Zone MPC technique are shown and described in Benyamin Grosman, Ph.D., Eyal Dassau, Ph.D., Howard C. Zisser, M.D., Lois Jovanoviě, M. D., and Francis J. Doyle III, Ph.D. "*Zone Model Predictive Control: A Strategy to Minimize Hyper and Hypoglycemic Events*" Journal of Diabetes Science and Technology, Vol. 4, Issue 4, July 2010, with a copy in the Appendix. Additional details of the Zone MPC are shown and described in US Patent Application Publication No. 20110208156 to Doyle et al., entitled "*Systems, Devices, and Methods to Deliver Biological Factors or Drugs to a Subject*," with the publication date of Aug. 25, 2011, which is incorporated by reference as if set forth. A related derivation of Zone MPC was presented in Maciejowski J M., "*Predictive Control with Constraints*", Harlow, UK: Prentice-Hall, Pearson Education Limited, 2002. The Zone MPC is implemented by defining fixed upper and lower bounds as soft constraints by letting the optimization weights switch between zero and some final values when the predicted CVs are in or out of the desired zone, respectively. The predicted residuals are generally defined as the difference between the CV that is out of the desired zone and the nearest bound. Zone MPC is typically divided into three different zones. The permitted range is the control target and it is defined by upper and lower bounds. The upper zone represents undesirable high predicted glycemic values. The lower zone represents undesirable low predicted glycemic values that represent hypoglycemic zone or a pre-hypoglycemic protective area that is a low alarm zone. The Zone MPC optimizes the predicted glycemia by manipulating the near-future insulin control moves to stay in the permitted zone under specified constrains.

The core of Zone MPC lies in its cost function formulation that holds the zone formulation. Zone MPC, like any other forms of MPC, predicts the future output by an explicit model using past input/output records and future input moves that need to be optimized. However, instead of driving to a specific fixed set point, the optimization attempts to keep or move the predicted outputs into a zone that is defined by upper and lower bounds. Using a linear difference model, the glycemic dynamics are predicted and the optimization reduces future glycemic excursions from the zone under constraints and weights defined in its cost function.

The Zone MPC cost function J used in the presented work is defined as follows:

$$J(I'_D) = Q \cdot \sum_{j=1}^{P} \|G^{zone}(k+j)\| + R \cdot \sum_{j=0}^{M-1} \|I'_D(k+j)\| \quad (3)$$

s.t.

$G(k+j) = f[G(k+j-1), I'_D(k+j-1)] \; \forall \; j = 1, P-$ $\text{basal}(k+j) \leq I'_D(k+j) \leq 72 \; \forall \; j = 0, M-1$ or for our applications:

$$J(I_D') = \Sigma \|G^{zone}(k+j)\| + R \cdot \Sigma \|I_D(k+j) - \text{basal}(k+j)\| \quad (4)$$

where
Q is a weighting factor on the predicted glucose term;
R is a tuning factor on the future proposed inputs in the cost function;
f is the prediction function (in Eq. (2));
vector $I_D$ contains the set of proposed near-future insulin infusion amounts. It is the "manipulated variable" because it is manipulated in order to find the minimum in J.
$G^{zone}$ is a variable quantifying the deviation of future model-predicted CGM values G outside a specified glycemic zone, and is determined by making the following comparisons:

$$G^{zone} = \begin{cases} 0 & \text{if } G_{ZL} \le G \le G_{ZH} \\ G - G_{ZH} & \text{if } G > G_{ZH} \\ G_{ZL} - G & \text{if } G < G_{ZL} \end{cases} \quad (5)$$

where the glycemic zone is defined by the upper limit $G_{ZH}$ and the lower limit $G_{ZL}$.

Thus, if all the predicted glucose values are within the zone, then every element of $G^{zone}$ is equal to 0, and consequently J is minimized with $I_D$=basal for that time of day, i.e., the algorithm "defaults" to the patient's current basal insulin infusion rate. On the other hand, if any of the predicted glucose values are outside the zone, then $G^{zone}>0$ and thus "contributes" to the cost function. In this case, the near-future proposed insulin infusion amounts $I_D$ will deviate from the basal in order to prevent out-of-zone deviation in $G^{zone}$ from ever happening, which will also "contribute" to the cost function. Then, a quantitative balance is found in the optimization, based on the weighting factor R.

In order to solve optimization problem of Equations (2)-(5), a commercially available software (e.g., MATLAB's "fmincon.m" function) is utilized. For this function, the following parameters are used for each optimization:

Initial guess for the insulin delivery rates, $I_D'(0)$, is the null vector $\vec{0} \in R^M$, e.g., if M=5 the initial guess for each optimization is $I_D' = [0\ 0\ 0\ 0\ 0]$. This implies that the initial guess is equivalent to the basal rate.

Maximum number of function evaluations allowed is Max_f=100*M, where M is control horizon as described earlier.

Maximum number of iterations is Max_i=400, which is fixed.

Termination on the cost function values Term_cost=1e-6, which is fixed.

Termination tolerance Term_tol on the manipulated variables $I_D'$ is 1e-6.

The following hard constraints are implemented on the manipulated variables ($I_D'$):

$$-\text{basal} \le I_D' \le 72 \text{ U/h} \quad (6)$$

where basal is the subject's basal rate as set by the subject or his/her physician,
expected in the range 0.6-1.8 U/hr.

Although the values of control horizontal parameter M and prediction horizon parameter P have significant effects on the controller performance, and are normally used to tune an MPC based controller, they can be heuristically tuned based on knowledge of the system. Tuning rules are known to those skilled in the field. According to these rules M and P may vary between:

$$2 \le M \le 10$$

$$20 \le P \le 120 \quad (7)$$

In the preferred embodiments, we use the nominal values of M=5 and P=108.

The ratio of the output error weighting factor Q and the input change weighting matrix or tuning factor R may vary between:

$$10 \le \frac{R}{Q} \le 1000 \quad (8)$$

In the preferred embodiments, we use the nominal value of R/Q=500.

Once the controller is initialized and switched on, real-time calculations take place every five minutes, corresponding to the sample time for the glucose sensor. The first element of $I_D$ is delivered as an insulin dose to the patient through the insulin pump, five minutes elapse, a new CGM reading becomes available, and the process repeats. It is noted that the future control moves are hard-constrained, set by the insulin pump's ability to deliver a maximum rate of insulin and the inability to deliver negative insulin values. Other details of related subject matter including state estimator, and other MPC are provided by Rachel Gillis et al., "*Glucose Estimation and Prediction through Meal Responses Using Ambulatory Subject Data for Advisory Mode Model Predictive Control*" Journal of Diabetes Science and Technology Vol. 1, Issue 6, November 2007 and by Youqing Wang et al., "*Closed-Loop Control of Artificial Pancreatic β-Cell in Type 1 Diabetes Mellitus Using Model Predictive Iterative Learning Control*" IEEE Transactions on Biomedical Engineering, Vol. 57, No. 2, February 2010, which are herby incorporated by reference into this application as if fully set forth herein.

Control-to-Target MPC Mode.

The control to target technique in the context of MPC is a simplification of the control to range method in which, effectively, the "range" is one CGM value, e.g., 110 mg/dL, and therefore has zero width. One realization of a control to target control law, based on the equations given above for the control-to-range technique, would be achieved by rewriting Eq. 5 as $$G^{zone} = G^{target} = |G - G_{sp}| \quad (9)$$

where the indicated norm is the absolute value, and $G_{sp}$ is the glucose set point, or target concentration, e.g., 110 mg/dL. In words, every predicted glucose value carries with it a (positive) penalty amount, unless it is exactly equal to the target $G_{sp}$.

In fact, the structure of the penalty for a glucose prediction might take different forms. As shown in Eq. 9, the penalty of a given predicted glucose value is equivalent to its absolute deviation from $G_{sp}$. However, it is straightforward to impose different penalty structures such that the penalty of a given predicted glucose value is equivalent to the square of its deviation from $G_{sp}$, for example.

Figure 3:
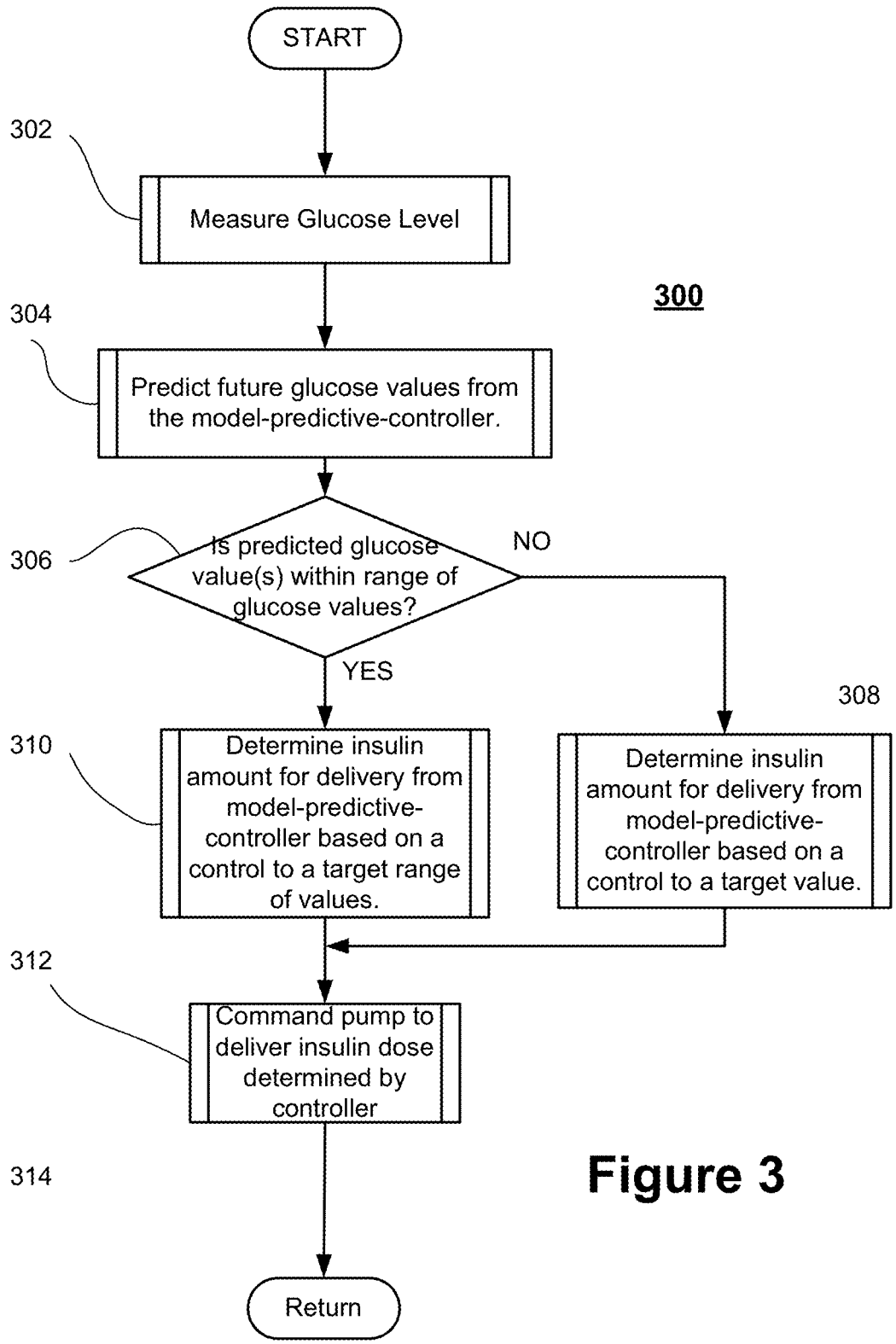
FIG. 3 illustrates the logic utilized in the controller of FIG. 1 or FIG. 2A.

Now that the CTR and CTT modes for MPC have been described, reference will be made to FIG. 3 in which applicants have devised a technique to determine which mode is best utilized to determine the appropriate insulin dosing. In FIG. 3, the technique 300 begins with the appropriate sensor (e.g., CGM sensor) measuring a glucose level in the subject to provide at least one glucose measurement in each time interval in a series of discrete time interval index ("k") at step 302. At step 304, the MPC controller 10 is utilized in a predicting of at least one future glucose value based on the glucose measurements made in the measuring step. At decision point 306, the system evaluates as to whether the at least one future glucose value is within a predetermined range of glucose values. In the event the at least one future glucose value is not within the range, (i.e., the decision step 306 returning a "no"), then a determination of an insulin amount with the model-predictive controller is made based on a target value, as described above. Otherwise, if the evaluation step 306 returns a yes, the logic moves to step 310 in which a determination is made of an insulin amount with the model-predictive-controller based on the predetermined range. At step 312, the system delivers the insulin in the amount determined in the determining step (i.e., step 308 or step 310).

In one implementation of this technique, a system is provided that includes a continuous glucose monitor 22, an insulin infusion pump 16, and a controller 10. The monitor 22 is configured to continuously measure glucose level of the subject 20 at discrete time intervals and provide the glucose level at each interval in the form of glucose measurement data. The pump is configured to deliver insulin to a subject. The controller is in communication with the pump, glucose meter and the glucose monitor. In this system, the controller is configured to: (a) predict at least one future glucose value based on prior glucose measurement data from the continuous glucose monitor 22, (b) evaluate whether the at least one future glucose value is within a predetermined range of glucose values and in the event the at least one future glucose value is not within the range, a determination is made of an insulin amount with the model-predictive controller based on a target value otherwise a determination is made of an insulin amount with the model-predictive-controller based on the predetermined range and (c) command the insulin infusion pump 16 to deliver the insulin amount determined by the controller.

The following examples will demonstrate applicant's new technique. Shown below are quantitative examples of this algorithm for two cases. In Case A, the initial glucose prediction (i.e., that obtained assuming basal insulin delivery for the future) is contained entirely within the glucose target range or zone. In Case B, the initial glucose prediction breaches the target range.

In the following example, the glucose target range is 90-140 mg/dL, and the subject's basal rate is 1 U/h. For Step 2 in Case B, the target glucose value (CTT set point) is 140 mg/dL.

TABLE A

Figure 4A:
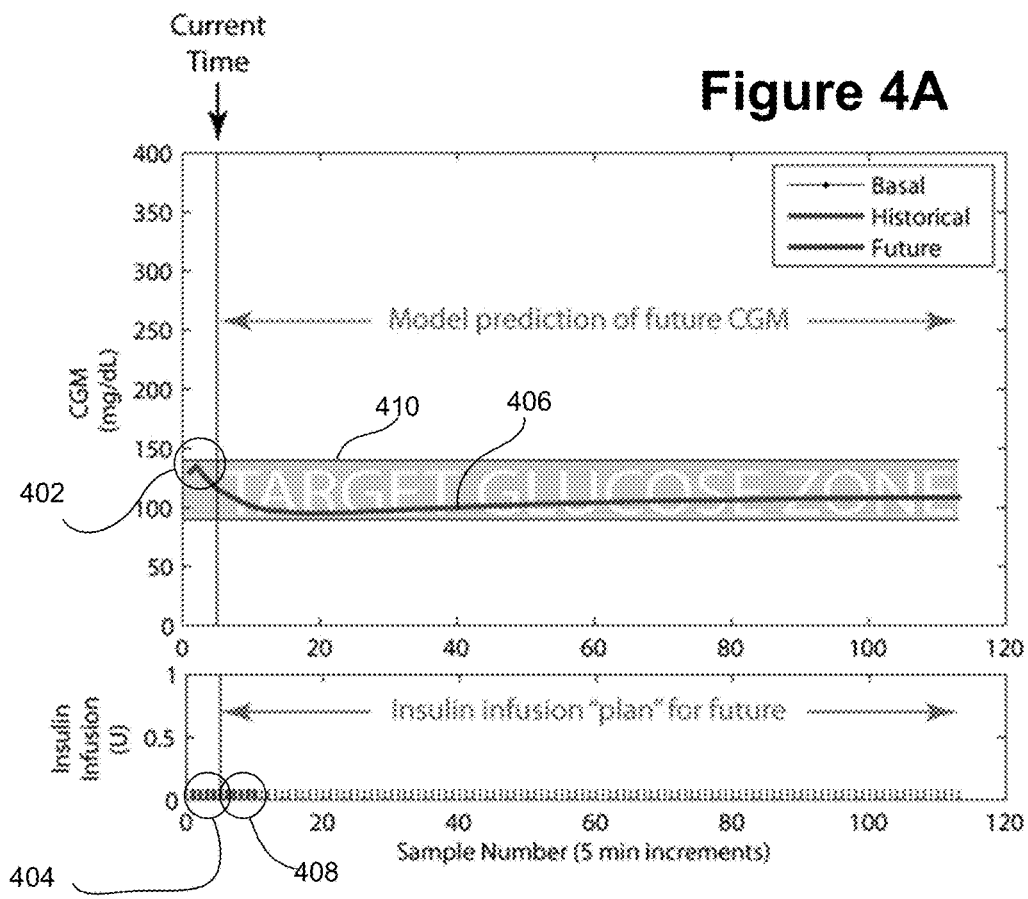
FIGS. 4A and 4B illustrate example A for a CTR-MPC mode.

The most recent five CGM values from oldest to newest is plotted at 402 in FIG. 4A.

130 mg/dL
135 mg/dL
128 mg/dL

TABLE A-continued

The most recent five CGM values from oldest to newest is plotted at 402 in FIG. 4A.

121 mg/dL
116 mg/dL

Figure 4B:
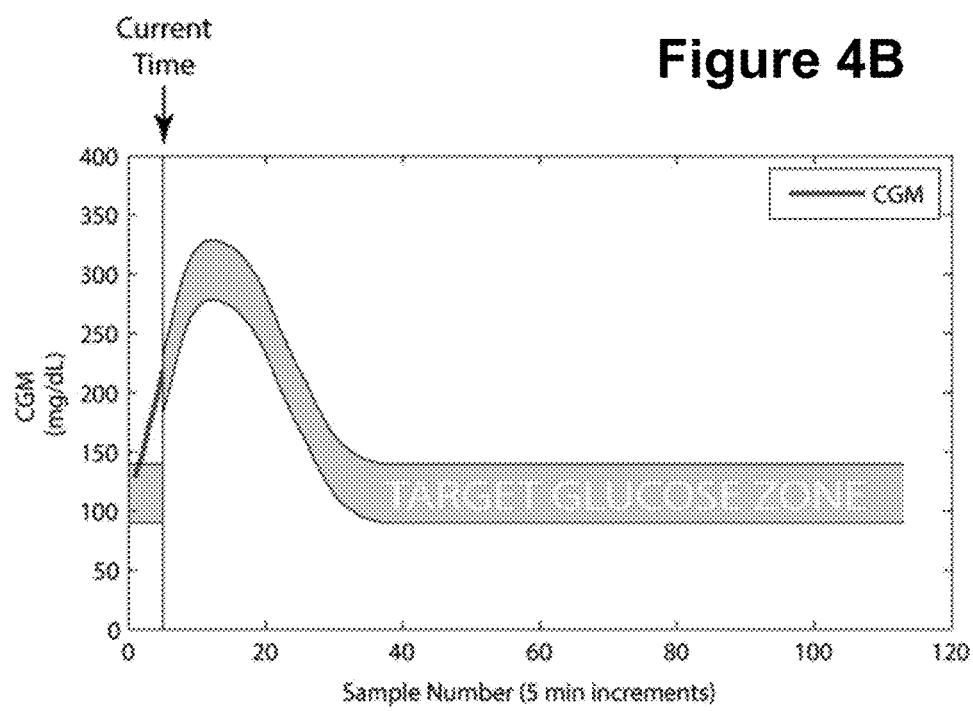

In FIG. 4A, the system has been delivering a basal dose of 1 U/h; which maps to a $\frac{1}{12}$ U injection every 5 minutes in the recent history at 404. The MPC controller 10 determines future or predicted blood glucose values 406 and shows that (assuming future basal delivery 408) there would likely be no breach by actual blood glucose value based on the predicted future blood glucose values 406. Hence, in accordance with step 306, if the predicted glucose 406 is within the target range 410, the basal insulin (in this case 1 U/h) is delivered. It is noted that for the example in FIG. 4A, the target zone can be generally constant. However, in certain configurations, the target zone can vary as shown here in FIG. 4B.

Figure 5A:
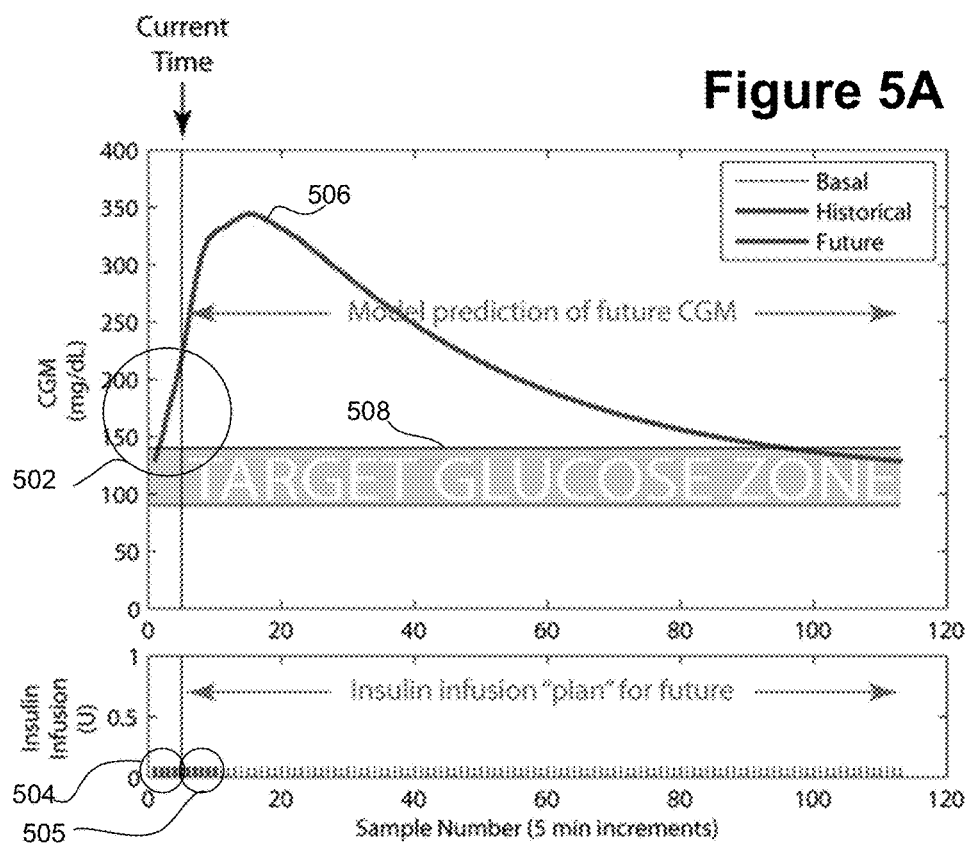
FIGS. 5A and 5B illustrate example B for a switchover from a CTR-MPC mode to a CTT-MPC mode.
Figure 5B:
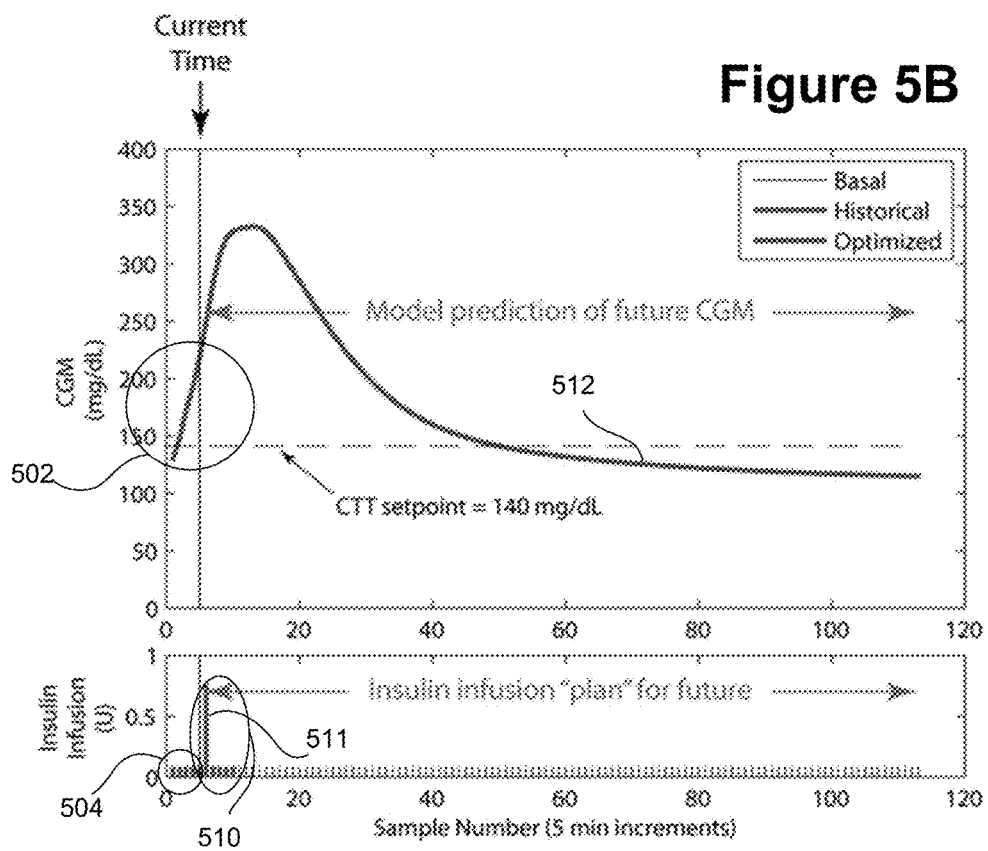

On the other hand, a switch from a CTR-MPC to CTT-MPC can be made under certain circumstances, as shown in FIGS. 5A and 5B in this example B. In Table B, the most recent CGM values from oldest to newest are provided.

TABLE B

The most recent five CGM values from oldest to newest are plotted at 502 in FIG. 5A.

130 mg/dL
148 mg/dL
173 mg/dL
193 mg/dL
218 mg/dL

As in the example A, the controller 10 in example B, has been commanding the pump to deliver a basal rate of 1 Units per hour (U/h) (or $\frac{1}{12}$ Unit every 5 minute at 504 in FIG. 5A. However, a prediction into the future by the MPC controller shows that (assuming the same basal insulin rate as before at 505), there would likely be a clear excursion of the blood glucose values 506 in the subject above the target zone 508. Hence, in accordance with the logic 300, at step 306, the evaluating step would return a "no" and the logic would switch over from a CTR mode to a CTT mode for the insulin dosing by the pump. For the purposes of this example B, it is assumed that the CTT set point is the upper limit of the target glucose zone or about 140 mg/dL. Consequently, the MPC controller will determine, in the CTT mode of FIG. 5B, the appropriate insulin infusion in the near future (e.g., the next five insulin infusion amounts) at 510 (with a sharp spike to 0.76 Unit at 511 followed by the previous basal amount of $\frac{1}{12}$ Unit) such that the predicted future glucose values 512 would trend sharply downward so as to be under the CTT set point of 140 mg/dL.

An investigation was made into the benefits of this new technique. Four different glucose scenarios were considered: two scenarios for hyperglycemia and two scenarios for hypoglycemia. To quantify computation requirements, quantifications of the number of iterations involved in the minimization routine, as well as the number of function evaluations in each of the known technique and the new technique as taught herein. Table C illustrates the different scenarios that were considered and the number of iterations and function evaluations that had to be considered under the known Zone MPC technique and under the new hybrid technique ("Hybrid CTT-CTR").

TABLE C

Evaluation between Zone MPC and the Hybrid CTT-CTR technique

| | Zone MPC | | | Hybrid CTT-CTR | | |
|---|---|---|---|---|---|---|
| | Iterations | Function Evaluations | Insulin Result (U, deviation from basal) | Iterations | Function Evaluations | Insulin Result (U, deviation from basal) |
| Scenario 1 - hyperglycemia #1 | 20 | 325 | 0.36 | 4 | 37 | 0.74 |
| Scenario 2 - hyperglycemia #2 | 39 | 503 | 0.78 | 4 | 36 | 1.25 |
| Scenario 3 - hypoglycemia #1 | 11 | 191 | −0.08 | 3 | 24 | −0.08 |
| Scenario 4 - hypoglycemia #2 | 20 | 330 | −0.05 | 4 | 31 | −0.08 |

As seen in Table D, there are significant improvements in the new hybrid switchover technique whereby the number of iterations in the controller to reach the commanded insulin dosing, for example, in Scenario 1, is 80% less and the number of function evaluations in the controller for the insulin dosing is 89% less. Based on these limited data for Table C, the new technique needed on average 80.6% fewer iterations, and 89.9% fewer function evaluations than the Zone MPC control schema. A caveat is that the methods can result in different insulin-delivery results, which are the outcome of the minimization routines. With proper tuning, which is well within the capabilities of one skilled in the art, this caveat is not believed to be an issue.

TABLE D

Improvements for Hybrid Technique to Zone MPC of Table C.

Improvement of Hybrid Technique relative to "Zone MPC" in Table C

| Iterations | Function Evaluations | |
|---|---|---|
| 80.0% | 88.6% | |
| 89.7% | 92.8% | |
| 72.7% | 87.4% | |
| 80.0% | 90.6% | |
| 80.6% | 89.9% | Avg. |

By virtue of the hybrid switchover technique, as taught herein, from the CTR mode in FIG. 5A to CTT mode in FIG. 5B, a reduction in processing time of is provided in the system. In other words, the time necessary for the MPC to determine the appropriate dosing in the CTR mode is reduced when the system switches over to CTT mode, thereby reducing power consumption, enabling the battery for the system to last significantly longer than before.

While the invention has been described in terms of particular variations and illustrative figures, those of ordinary skill in the art will recognize that the invention is not limited to the variations or figures described. For example, the closed-loop controller need not be an MPC controller but can be, with appropriate modifications by those skilled in the art, a PID controller, a PID controller with internal model control (IMC), a model-algorithmic-control (MAC) that are discussed by Percival et al., in "*Closed-Loop Control and Advisory Mode Evaluation of an Artificial Pancreatic β Cell: Use of Proportional-Integral-Derivative Equivalent Model-Based Controllers*" Journal of Diabetes Science and Technology, Vol. 2, Issue 4, July 2008. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well.

What is claimed is:

1. A method to control a glucose management system having an infusion pump with a model-predictive-controller that receives data from at least one glucose sensor and which the model-predictive controller has a control-to-target operating mode in which the model-predictive controller is configured to maintain glucose at a specific target value and a control-to-range operating mode in which the model-predictive controller is configured to maintain glucose within a target range of values, the method comprising:

initially engaging the model-predictive controller in the control-to-range operating mode;

measuring glucose level in the subject from the at least one glucose sensor to provide at least one glucose measurement in each time interval in a series of discrete time interval index;

using the model-predictive controller in the control-to-range operating mode to predict at least one future glucose value based on the glucose measurements made in the measuring step;

using the model-predictive controller to evaluate whether the at least one future glucose value is within the target range of glucose values for the control-to-range operating mode;

configuring the model-predictive controller based on evaluation of the at least one predicted future glucose value to:

(i) maintain the model-predictive controller in the control-to-range operating mode if the at least one predicted future glucose value is within the target range of glucose values for the control-to-range operating mode and determining an insulin amount with the model-predictive controller using the control-to-range operating mode wherein a cost function is calculated using the model-predictive controller based on deviation of the at least one predicted future glucose value from the target range of glucose values; and (ii) shift the model-predictive-controller from the control-to-range operating mode to the control-to-target operating mode and determining an insulin amount with the model-predictive-controller in the control-to-target operating mode when the at least one predicted future glucose value is outside the target range of glucose values wherein a cost function is calculated using the model-predictive controller based on deviation of the at least one predicted future glucose value from a specific target glucose value; and delivering the insulin in the amount determined, wherein the cost function is defined as:

$$J(I'_D) = Q \cdot \sum_{j=1}^{P} \|G^{zone}(k+j)\| + R \cdot \sum_{j=0}^{M-1} \|I'_D(k+j)\|$$

s.t.

$$G(k+j) = f[G(k+j-1), I'_D(k+j-1)] \forall\ f = 1,$$

$$P - \text{basal}(k+j) \le I'_D(k+j) \le 72 \forall\ j = 0, M-1,$$

where:
J is the cost function;
$I_D'$ is an insulin infusion rate ($I_D$) deviation variable (U/h), i.e., $I_D' \equiv I_D$–basal U/h;
k is the discrete time interval index having a series of indexing counters where k=1, 2, 3 . . . ;
Q is a weighting factor on a predicted glucose term;
R is a tuning factor on future proposed inputs in the cost function;
f is a prediction function;
vector $I_D$ contains a set of proposed near-future insulin infusion amounts, manipulated to find a minimum J; and
$G^{zone}$ is a variable quantifying the deviation of the at least one future glucose value G outside a specified glycemic zone.

2. The method of claim 1, in which the measuring comprises assaying glucose values with a continuous glucose sensor.

3. The method of claim 1, in which the delivering comprises injecting the insulin with an insulin infusion pump.

4. The method of claim 1, in which the target range varies over time.

5. The method of claim 1, wherein, when the insulin amount is determined with the model-predictive controller using the control-to-range operating mode, when the at least one predicted glucose value falls within the target range of glucose values, there is no penalty contribution to the cost function and when the at least one predicted glucose value falls outside the target range of glucose values, there is an increasing penalty contribution to the cost function based on a weighting factor.

6. The method of claim 1, wherein, when the insulin is determined with the model-predictive-controller in the control-to-target operating mode, a penalty contribution to the cost function is equivalent to deviation from the target glucose value.

7. The method of claim 1, wherein the cost function is further defined as:

$$J(I_D') = \Sigma \|G^{zone}(k+j)\| + R \cdot \Sigma \|I_D(k+j) - \text{basal}(k+j)\|.$$

8. The method of claim 1, wherein, in the control-to-range operating mode, $G^{zone}$ is determined as:

$$G^{zone} = \begin{cases} 0 & \text{if } G_{ZL} \le G \le G_{ZH} \\ G - G_{ZH} & \text{if } G > G_{ZH} \\ G_{ZL} - G & \text{if } G < G_{ZL} \end{cases},$$

where the glycemic zone is defined by the upper limit $G_{ZH}$ and the lower limit $G_{ZL}$.

9. The method of claim 1, wherein, in the control-to-range operating mode, $G^{zone}$ is determined as:

$$G^{zone} = G^{target} = |G - G_{sp}|,$$

where $G_{sp}$ is the target glucose value.

10. The method of claim 1, wherein, in the control-to-range operating mode, $G^{zone}$ is determined as:

$$G^{zone} = G^{target} = (G - G_{sp})^2,$$

where $G_{sp}$ is the target glucose value.

11. A system for management of diabetes comprising:
a continuous glucose monitor to continuously measure glucose level of the subject at discrete generally uniform time intervals and provide the glucose level at each interval in the form of glucose measurement data;
an insulin infusion pump to deliver insulin; and
a model-predictive controller in communication with the infusion pump and the continuous glucose monitor in which the model-predictive controller is configured to operate in two separate operating modes; namely, a control-to-range operating mode in which the model-predictive controller is configured to maintain glucose within a target range of values and a control-to-target operating mode in which the model-predictive controller is configured to maintain glucose at a specific target value,
wherein the model-predictive controller is further configured to predict at least one future glucose value based on prior glucose measurement data from the continuous glucose monitor while in the control-to-range operating mode, evaluate whether the at least one future glucose value is within the target range of glucose values in which the model-predictive controller is configured to operate and control insulin amounts in each of the two operating modes based on evaluation of the at least one future glucose value,
the model-predictive controller being maintained in the control-to-range operating mode if the predicted at least one future glucose value is within the target range of values and being configured to calculate a cost function based on deviation of the at least one predicted future glucose value from the target range of glucose values and the model-predictive controller being automatically shifted to the control-to-target operating mode in which the model-predictive controller is configured to calculate a cost function based on deviation from a target glucose value if the predicted at least one future glucose value is outside of the target range of values, wherein the model-predictive controller determines an insulin amount to be delivered depending on the operating mode and commands the insulin infusion pump to deliver the insulin amount determined by the model-predictive controller wherein calculated amounts of insulin are delivered at predetermined time intervals based on future predicted glucose values in each operating mode wherein the cost function is defined as:

$$J(I_D') = Q \cdot \sum_{j=1}^{P} \|G^{zone}(k+j)\| + R \cdot \sum_{j=0}^{M-1} \|I_D'(k+j)\|$$

s.t.

$$G(k+j) = f[G(k+j-1), I_D'(k+j-1)] \forall f = 1,$$

$$P - \text{basal}(k+j) \le I_D'(k+j) \le 72 \forall j = 0, M-1,$$

where:
J is the cost function;
$I_D'$ is an insulin infusion rate ($I_D$) deviation variable (U/h), i.e., $I_D' \equiv I_D$–basal U/h;
k is the discrete time interval index having a series of indexing counters where k=1, 2, 3 . . . ;
Q is a weighting factor on a predicted glucose term;
R is a tuning factor on future proposed inputs in the cost function;
f is a prediction function;
vector $I_D$ contains a set of proposed near-future insulin infusion amounts, manipulated to find a minimum J; and
$G^{zone}$ is a variable quantifying the deviation of the at least one future glucose value G outside a specified glycemic zone.

12. The system of claim 11, in which the target range varies over time.

13. The method of claim 11, wherein, when the insulin amount is determined with the model-predictive controller using the control-to-range operating mode, when the at least one predicted glucose value falls within the target range of glucose values, there is no penalty contribution to the cost function and when the at least one predicted glucose value falls outside the target range of glucose values, there is an increasing penalty contribution to the cost function based on a weighting factor.

14. The method of claim 11, wherein, when the insulin is determined with the model-predictive-controller in the control-to-target operating mode, a penalty contribution to the cost function is equivalent to deviation from the target glucose value.

15. The method of claim 11, wherein the cost function is further defined as:

$$J(I_D') = \Sigma \|G^{zone}(k+j)\| + R \cdot \Sigma \|I_D'(k+j) - \text{basal}(k+j)\|.$$

16. The method of claim 11, wherein, in the control-to-range operating mode, $G^{zone}$ is determined as:

$$G^{zone} = \begin{cases} 0 & \text{if } G_{ZL} \le G \le G_{ZH} \\ G - G_{ZH} & \text{if } G > G_{ZH} \\ G_{ZL} - G & \text{if } G < G_{ZL} \end{cases},$$

where the glycemic zone is defined by the upper limit $G_{ZH}$ and the lower limit $G_{ZL}$.

17. The method of claim 11, wherein, in the control-to-range operating mode, $G^{zone}$ is determined as:

$$G^{zone} = G^{target} = |G - G_{sp}|,$$

where $G_{sp}$ is the target glucose value.

18. The method of claim 11, wherein, in the control-to-range operating mode, $G^{zone}$ is determined as:

$$G^{zone} = G^{target} = (G - G_{sp})^2,$$

where $G_{sp}$ is the target glucose value.

* * * * *